United States Patent
Raghupathi et al.

(10) Patent No.: US 6,696,417 B1
(45) Date of Patent: Feb. 24, 2004

(54) SKIN AND HAIR DARKENING COMPOSITION

(75) Inventors: Subramanian Raghupathi, Mumbai (IN); Abburi Ramaiah, Dehradun (IN); Govindarajan Raman, Bangalore (IN); Sushama Shripad Wagh, Bangalore (IN)

(73) Assignee: Chesebrough-Pond's USA Co., division of Conopco, Inc., Greenwich, CT (US)

( * ) Notice: Subject to any disclaimer, the term of this patent is extended or adjusted under 35 U.S.C. 154(b) by 99 days.

(21) Appl. No.: 09/191,974

(22) Filed: Nov. 13, 1998

(30) Foreign Application Priority Data

Nov. 21, 1997 (IN) ........................ 684/BOM/97
Jan. 20, 1998 (GB) ............................. 9801191

(51) Int. Cl.⁷ ............................... A61K 38/00
(52) U.S. Cl. ........................ 514/17; 514/2; 514/880; 514/844; 424/59; 424/70.1; 424/70.6
(58) Field of Search ............... 514/2, 17, 880, 514/844; 424/59, 70.1, 70.6

(56) References Cited

U.S. PATENT DOCUMENTS

| | | | | |
|---|---|---|---|---|
| 4,186,188 A | * | 1/1980 | Gumprecht | ................. 424/70 |
| 4,732,692 A | * | 3/1988 | Zabotto et al. | ............. 252/106 |
| 4,866,038 A | | 9/1989 | Hruby et al. | .................. 514/14 |
| 4,918,055 A | | 4/1990 | Hruby et al. | .................. 514/14 |
| 5,075,102 A | * | 12/1991 | Hubaud et al. | ................ 424/59 |
| 5,620,681 A | * | 4/1997 | Takata et al. | ................. 424/59 |
| 5,683,981 A | * | 11/1997 | Hadley et al. | ................ 514/11 |

FOREIGN PATENT DOCUMENTS

| | | |
|---|---|---|
| EP | 0 293 837 | 12/1988 |
| FR | 2 608 424 | 12/1986 |
| WO | 89/05629 | 6/1989 |
| WO | 95/08564 | 3/1995 |

OTHER PUBLICATIONS

CAPLUS DN 123:311194, Vijayasaradhi et al., J. Cell Biol. (1995), 130(4), 807–20.*
Roberts et al., Basic Principles of Organic Chemistry, Second Edition, W.A Benjamin, Inc., 1977.*
WPI Abstract No. 98–042589/199805 & AU 9723507.
WPI Abstract No. 94–001646/199401 & FR 2691465.

* cited by examiner

Primary Examiner—Dwayne C. Jones
Assistant Examiner—C. Delacroix-Muirheid
(74) Attorney, Agent, or Firm—Milton L. Honig

(57) ABSTRACT

A cosmetic skin/hair darkening composition for topical application to skin and/or hair is provided that comprises for 0.1 to 10% by weight of a peptide having an isoelectric point ranging from 6 to 11.

13 Claims, No Drawings

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial
      Sequence:Hexapeptide(text)

<400> SEQUENCE: 1

Asx Gln Pro Leu Leu Thr
 1               5
```

SKIN AND HAIR DARKENING COMPOSITION

BACKGROUND OF THE INVENTION

1. Field of the Invention

The present invention relates to a cosmetic composition for darkening the skin and/or hair. The invention also relates to a method of topically applying to the skin and/or hair a skin/hair darkening composition according to the invention.

2. The Related Art

Skin tanning by UV exposure is a well known phenomenon. However, it is also well known from the literature that such exposure to UV radiation results in accelerated aging of skin and increased incidence of skin cancer. Accordingly, alternative modes of skin tanning have evolved. It is presently known in the art to use dihydroxy acetone (DHA) as a non-UV induced tanning aid. However, undesirably, the use of dihydroxy acetone for skin tanning purposes produces a rather unnatural looking sun tan. Further, the artificial tan produced by DHA does not protect against UV irradiation as would a natural tan.

Melanin is the black pigment of hair and skin and is synthesized from the amino acid tyrosine by melanosomes. Melanosomes are organelles found in melanocytes, a cell type present at dermis-epidermis junction. Tyrosine is acted upon by an enzyme, tyrosinase, which is the key step in melanogenesis.

In the melanosomes the melanin is synthesized from monomers and is transferred to the neighbouring cells called keratinocytes. The keratinocytes divide and differentiate and thus transport the melanosome to the surface of the skin. The intensity of the skin colour is directly related to the number, the size, melanin content, the rate of formation and migration/transfer of melanosomes to keratinocytes.

Several specific sequences of polyaminoacids and peptide residues are known to inhibit melanin pigmentation and have a whitening effect on the skin (JP 6345797; JP 6321757; JP 6321755; JP5170636; U.S. Pat. No. 5,126,327).

The peptides described in the prior art comprise a high proportion of basic and hydrophobic amino acids and have isoeletric point (pI) values greater than 5.5. These are mainly used for lightening the hyperpigmented areas associated with abnormal skin conditions.

The applicants in their co-pending British patent application 9719195.1, disclose a cosmetic composition for lightening the skin comprising from 0.1 to 10% by weight of a peptide with an isoelectric point of between 2 and 5.5. Isoelectric point (pI) is defined as the pH at which net charge on a molecule is zero. Peptides having large number of acidic amino acids like glutamic acid, aspartic acid etc. have a low pI and those having basic amino acids like lysine, arginine, histidine have a high pI.

DETAILED DESCRIPTION OF THE INVENTION

The Applicants have found that a composition comprising peptide sequences having a isoelectric point (pI) of between 6 and 11 is capable of darkening the skin/hair.

Accordingly, the present invention relates to a cosmetic skin/hair darkening composition comprising from 0.1% to 10% by weight of a peptide with an isoelectric point (pI) ranging from 6.0 to 11.

The skin/hair darkening effected by the composition of the invention is reversible and without any side effects. The composition according to the invention is active during both day and night.

The peptide is a sequence of amino acids and is of molecular weight ranging from 200 to 20,000 daltons (Da) with a pI ranging from 6.0 to 11.0. The peptide is also optionally linked to a hydrophobic amino acid or a targeting molecule or vehicle.

The amino acid residues forming the peptide sequence can be naturally occurring or synthetic, dextro or levo form, and includes any derivative thereof. The peptide sequence must comprise a proportion of the basic amino acids such that the resulting peptide is basic in nature. The peptide sequence may be straight chain or cyclic.

The molecular weight of the peptide sequence ranges from 200 to 20,000 Da and preferably from 200 to 2000 Da.

The pI of the peptide sequence ranges from 6.0 to 11.0.

The hydrophobic amino acid can be chosen from any one of alanine, isoleucine, leucine, methionine, phenyl alanine, proline, tryptophan or valine and is preferably tryptophan. The targeting molecule is preferable a peptide and most preferably a hexapeptide preferably having the primary sequence disclosed in SEQ ID NO: 1 and is located within 27 amino acid residue from the carboxy terminal of the active peptide. Targeting vehicles such as micelles and/or reverse micelles, may also be used.

According to a preferred aspect of the invention there is provided a cosmetic skin/hair darkening composition comprising from 0.5 to 5.0% by weight of the peptide.

The invention further relates to a cosmetic method of darkening skin/hair comprising topically applying to the skin and/or hair a composition according to the invention. The composition may also comprise a skin tanning agent. This tanning agent may be chosen from any known agent for this purpose such as dihydroxy acetone, theophyllin, copper gluconate, natural actives obtained from *Pterocarpus santalinus*, and any other known skin tanning agents.

The composition according to the invention may also comprise a cosmetically compatible carrier. It may also comprise preservatives, emulsifiers, thickeners, perfume, colour, skin benefit materials such as moisturisers, emollients and antiageing compounds.

The vehicle which forms part of the cosmetic composition is one or more substances which are compatible with the polyamino acid sequence and which are also cosmetically acceptable in that they will not harm the skin/hair. The vehicles that can be used in the compositions according to the invention can include powder absorbents, binders and carriers, and liquids such as emollients, propellants, solvents, humectants and thickeners. Also simple vehicles such as alcohol, PEG, propylene glycol may also be used.

Examples of moisturisers and humectants include polyols, glycerol, cetyl alcohol, carbopol 934, ethoxylated castor oil, paraffin oils, lanolin and its derivatives. Silicone compounds such as silicone surfactants like DC3225C (Dow Corning) and/or silicone emollients, silicone oil (DC-200 Ex-Dow Corning) may also be used.

The compositions according to the invention may be prepared for topical application to the skin/hair in the form of simple solutions or conventional leave-on or wash-off products such as lotions, creams, ointments, shampoos and/or aerosol products.

All percentages referred to herein and in the appended claims are by weight of the composition unless otherwise indicated.

The invention will now be illustrated by way of Examples. The Examples are for illustration only and do not in any way restrict the scope of the invention.

EXAMPLE 1

In vitro Demonstration of Enhancement of Melanin Formation

The influence of a peptide sequence with pI 11.0 on the formation of melanin at pH 5 in an in vitro system, comparable to the pH of the melanosomal system, was analysed. The assay conditions for the formation of melanin under in vitro conditions are as follows.

Assay Method

The control assay mixture contained 5 pmoles of DL-DOPA (Dihydroxy phenyl alanine), 20nmoles lysozyme and 3.2 units of tyrosinase in acetate buffer pH 5.0 in a test tube. A unit is defined as the amount of tyrosinase needed to convert 1 nmol DOPA in one minute. In the experimental set 11 nmoles of polylysine, a polyamino acid sequence with pI 11.0, was used in addition to the other ingredients as defined in the control. The melanin formed was washed with the acetate buffer, suspended in 1N sodium hydroxide and dissolved by heating the sample at 60° C. for 5 minutes. The absorbance was measured at 400 nm.

TABLE 1

| Sample | Melanin formed A 400 |
|---|---|
| Control | 0.120 |
| In presence of polylysine | 0.168 |

The above results show that in the presence of polylysine sequence the melanin production is significantly enhanced.

The invention will now be illustrated by reference to the following example of a cosmetic cream.

| Composition % Wt. | Comparative Example | EXAMPLE 2 |
|---|---|---|
| Stearic acid | 2.5 | 2.5 |
| Cetyl alcohol | 0.2 | 0.2 |
| Silicone oil | 0.5 | 0.5 |
| Isopropyl myristate | 2.0 | 2.0 |
| Glyceryl monostearate | 1.5 | 1.5 |
| Methyl/Propyl paraben | 0.3 | 0.3 |
| Glycerine | 1.0 | 1.0 |
| EDTA disodium salt | 0.04 | 0.04 |
| Light paraffin oil | 1.5 | 1.5 |
| Triethanolamine | 0.5 | 0.5 |
| Carbopol 941 | 0.5 | 0.5 |
| Dihydroxy acetone | 2.0 | 2.0 |
| Perfume | 0.3 | 0.3 |
| Polyamino acid (pI6-11) | — | 5.0 |
| Water | to 100 | to 100 |

Application of the cosmetic cream described in the Comparative Example and Example 2 will show that the product described in Example 2 will be significantly superior in darkening the skin to that of the Comparative Example.

It is thus possible by way of the present invention to provide for a skin/hair darkening composition which is reversible and without any side effects. The composition is active both during day and night.

The figures in the table represent percentages of the composition by weight.

EXAMPLE 3

In vitro Demonstration of Enhancement of Melanin Formation

The influence of the polyamino acid sequence with polyglutamate pI 2.5, polyarginine (pI 10.9) or polylysine (pI 11.0) on the formation of melanin at pH 5 in an in vitro system, comparable to the pH of the melanosomal system, was analysed. The assay conditions for the formation of melanin under in vitro conditions are as follows.

Assay Method:

The control assay mixture contained 5 mmoles of DL-DOPA (Dihydroxy phenyl alanine), lysozyme 20 nmoles and 0.45 mg of tyrosinase in acetate buffer pH 5.0 in a test tube. In the experimental set 18 nmoles of the polyglutamate, a polyamino acid sequence with pI 2.5 or polyarginine pI 10.9 or polylysine pI 11.0 was used in addition to the other ingredients as defined in the control. The melanin formed was washed with the buffer, suspended in 1 N sodium hydroxide and dissolved by heating the sample at 60° C. for 5 minutes. The absorbance was measured at 400 nm.

TABLE 2

| Sample | Melanin formed A 400 |
|---|---|
| Control | 0.120 |
| In presence of polyglutamate pI 3-4 | 0.048 |
| In presence of polylysine pI 11.0 | 0.168 |
| In presence of polyarginine pI 10.9 | 0.182 |

The above results show that in the presence of polyamino acid sequence with alkaline pI or pI>5.0 the melanin production is significantly enhanced whereas in the presence of polyamino acid sequence with pI in the acidic range we do not get a similar enhancement in melanin production.

EXAMPLE 4

In vivo Demonstration of Enhancement of Melanin Formation

Twelve female volunteers having even-toned skin and with no scars/visible hair on the forearms were chosen. On the volar side of the forearm 1 square cm. sites were marked using a template. A mixture of peptides of a molecular weight ranging from 14 K daltons, having a pI 11.2 at a concentration of 2% in a suitable vehicle was used. The above solution contained 0.3 µg protein/µl and 5 ml of this was applied for ten days. The untreated and placebo (Vehicle) served as controls. The sites were graded by an expert, who was blinded to the treatment assignments, on zero day and on 11th day. The data is presented in table 3 shows that even under in vivo conditions peptides with a pI>5.0 darken the skin significantly as compared to the two controls, namely the untreated and vehicle. The critical difference being 0.12.

TABLE 3

| Treatment | Mean change in skin score |
|---|---|
| Control (untreated) | −0.10 ± 0.220 |
| Control (vehicle) | 0.050 ± 0.063 |
| 5% Alkaline peptide | 0.360 ± 0.074 |

Legends for Expert Evaluation:
SUBSTANTIALLY LIGHTENED −1.0
DIFINITELY LIGHTENED −0.75
MODERATELY LIGHTENED −0.5
SLIGHTLY LIGHTENED −0.25
NO DIFFERENCE 0
SUBSTANTIALLY DARKENED +1.0
DIFINITELY DARKENED +0.75
MODERATELY DARKENED +0.5
SLIGHTLY DARKENED +0.25

What is claimed is:

1. A cosmetic composition comprising:
   (i) from 0.1 to 10% by weight of a peptide having an isoelectric point ranging from 6 to 11;
   (ii) an effective amount for tanning of an agent selected from the group consisting of dihydroxy acetone, theophylline, copper gluconate, and natural actives obtained from *Pterocarpus santalinus*; and
   (iii) a cosmetically compatible carrier.

2. The composition according to claim 1 wherein the agent is dihydroxy acetone.

3. The composition according to claim 1 wherein the peptide ranges in amount from 0.5 to 5.0% by weight.

4. The composition according to claim 1 wherein the peptide has a molecular weight of from 200 to 20,000 Da.

5. The composition according to claim 1 wherein the peptide is polylysine.

6. The composition according to claim 1 wherein the peptide is polyarginine.

7. A method for darkening skin comprising applying to the skin a composition comprising:
   (i) from 0.1 to 10% by weight of a peptide having an isoelectric point ranging from 6 to 11;
   (ii) an effective amount for tanning of an agent selected from the group consisting of dihydroxy acetone, theophylline, copper gluconate, and natural actives obtained from *Pterocarpus santalinus*; and
   (iii) a cosmetically compatible carrier.

8. The method according to claim 7 wherein the agent is dihydroxy acetone.

9. The method according to claim 7 wherein the peptide ranges in amount from 0.5 to 5.0% by weight.

10. The composition according to claim 7 wherein the peptide has a molecular weight of from 200 to 20,000 Da.

11. The composition according to claim 7 wherein the peptide is polylysine.

12. The composition according to claim 7 wherein the peptide is polyarginine.

13. A composition according to claim 1 wherein the peptide is attached to either:
   a) a hydrophobic amino acid selected from the group consisting of alanine, isoleucine, leucine, methionine, phenylalanine, valine, proline and tryptophan; or
   b) a targeting molecule or vehicle, and wherein the targeting molecule is a hexapeptide having the primary SEQ ID NO: 1.

\* \* \* \* \*